US012708658B2

(12) United States Patent
Zhou

(10) Patent No.: US 12,708,658 B2
(45) **Date of Patent: *Aug. 18, 2026**

(54) COMPOSITIONS AND METHODS FOR TREATING HEART FAILURE

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/784,736

(22) Filed: Jul. 25, 2024

(65) Prior Publication Data

US 2024/0366725 A1 Nov. 7, 2024

Related U.S. Application Data

(60) Continuation of application No. 17/576,886, filed on Jan. 14, 2022, now Pat. No. 12,076,370, which is a continuation of application No. 15/397,623, filed on Jan. 3, 2017, now Pat. No. 11,253,573, which is a division of application No. 14/350,050, filed as application No. PCT/CN2012/001354 on Oct. 8, 2012, now abandoned.

(30) Foreign Application Priority Data

Oct. 10, 2011 (WO) ................ PCT/CN2011/001691
Nov. 2, 2011 (WO) ................ PCT/CN2011/081699

(51) Int. Cl.

*A61K 38/18* (2006.01)
*A61K 9/00* (2006.01)
*A61K 45/06* (2006.01)
*C07K 14/475* (2006.01)
*G01N 33/68* (2006.01)
*G01N 33/74* (2006.01)

(52) U.S. Cl.

CPC ........ *A61K 38/1883* (2013.01); *A61K 9/0019* (2013.01); *A61K 45/06* (2013.01); *C07K 14/4756* (2013.01); *G01N 33/6893* (2013.01); *G01N 33/74* (2013.01); *G01N 2333/58* (2013.01); *G01N 2800/325* (2013.01); *G01N 2800/52* (2013.01)

(58) Field of Classification Search

None

See application file for complete search history.

(56) References Cited

U.S. PATENT DOCUMENTS 3,773,919 A 11/1973 Boswell et al.
4,179,337 A 12/1979 Davis et al.
4,301,144 A 11/1981 Iwashita et al.
4,485,045 A 11/1984 Regen
4,496,689 A 1/1985 Mitra
4,544,545 A 10/1985 Ryan et al.
4,640,835 A 2/1987 Shimizu et al.
4,670,417 A 6/1987 Iwasaki et al.
4,736,866 A 4/1988 Leder et al.
4,791,192 A 12/1988 Nakagawa et al.
4,870,009 A 9/1989 Evans et al.
4,873,191 A 10/1989 Wagner et al.
4,946,778 A 8/1990 Ladner et al.
4,980,286 A 12/1990 Morgan et al.
5,225,539 A 7/1993 Winter
5,272,065 A 12/1993 Inouye et al.
5,367,060 A 11/1994 Vandlen et al.
5,585,089 A 12/1996 Queen et al.
5,586,110 A 12/1996 Nakaki et al.
5,641,869 A 6/1997 Vandlen et al.
5,667,780 A 9/1997 Ho et al.
5,686,102 A 11/1997 Gross et al.
5,714,385 A 2/1998 Mather et al.
5,716,930 A 2/1998 Goodearl et al.
5,721,139 A 2/1998 Mather et al.
5,736,154 A 4/1998 Fuisz
5,741,511 A 4/1998 Lee et al.
5,834,229 A 11/1998 Vandlen et al.
5,840,525 A 11/1998 Vandlen et al.
5,840,697 A 11/1998 Blondelle et al.
5,846,720 A 12/1998 Foulkes et al.

(Continued)

FOREIGN PATENT DOCUMENTS

AU 68278/94 A 11/1994
CN 1276381 A 12/2000

(Continued)

OTHER PUBLICATIONS

Bakalets, "Chronic heart deficiency with preserved left ventricle ejection fraction," Problems of Health and Ecology, Gomel State Medical University, 3(33):7-11 (2012). English abstract.

(Continued)

*Primary Examiner* — Christine J Saoud
*Assistant Examiner* — Jon M Lockard
(74) *Attorney, Agent, or Firm* — Jones Day

(57) ABSTRACT

The present invention provides methods for treating chronic heart failure patients using the medication comprising neuregulin. The methods comprise first performing a companion diagnostic test of each patient before treatment; and then providing a suitable treatment to the patient according to the results of the companion diagnostic test. When the result of the test is within a favorite treatment zone, the patient is suitable for heart failure treatment by administering an effective amount of neuregulin.

8 Claims, No Drawings

Specification includes a Sequence Listing.

(56) References Cited

U.S. PATENT DOCUMENTS 5,856,110 A 1/1999 Vandlen et al.
5,859,206 A 1/1999 Vandlen et al.
5,886,039 A 3/1999 Kock et al.
5,906,810 A 5/1999 Turner
5,941,868 A 8/1999 Kaplan et al.
5,968,511 A 10/1999 Akita et al.
6,033,660 A 3/2000 Mather et al.
6,054,261 A 4/2000 Masterson
6,087,323 A 7/2000 Gwynne et al.
6,096,873 A 8/2000 Schaefer et al.
6,121,415 A 9/2000 Godowski et al.
6,136,558 A 10/2000 Ballinger et al.
6,156,728 A 12/2000 Gao et al.
6,162,641 A 12/2000 Goldman et al.
6,169,070 B1 1/2001 Chen et al.
6,197,801 B1 3/2001 Lin
6,252,051 B1 6/2001 Godowski et al.
6,258,374 B1 7/2001 Friess et al.
6,387,638 B1 5/2002 Ballinger et al.
6,399,746 B1 6/2002 Vandlen et al.
6,444,642 B1 9/2002 Sklar et al.
6,589,229 B1 7/2003 Connelly et al.
6,593,290 B1 7/2003 Gao et al.
6,635,249 B1 10/2003 Marchioni et al.
6,750,196 B1 6/2004 Reh et al.
7,037,888 B1 5/2006 Sklar et al.
7,063,961 B2 6/2006 Ballinger et al.
7,115,554 B1 10/2006 Sklar et al.
7,226,907 B1 6/2007 Zhou
7,612,164 B2 11/2009 Zhou
7,686,787 B2 3/2010 Moberg et al.
7,795,212 B2 9/2010 Zhou
7,919,098 B2 4/2011 Zhou
7,964,555 B2 6/2011 Zhou
8,394,761 B2 3/2013 Marchionni et al.
8,476,405 B2 7/2013 Zhou
8,609,620 B2 12/2013 Zhou
8,785,387 B2 7/2014 Zhou
9,012,400 B2 4/2015 Zhou
9,089,524 B2 7/2015 Zhou
9,198,951 B2 12/2015 Caggiano et al.
9,340,597 B2 5/2016 Zhou
9,434,777 B2 9/2016 Zhou
9,555,076 B2 1/2017 Zhou
9,580,515 B2 2/2017 Zhou
9,592,339 B2 3/2017 Zhou
9,655,949 B2 5/2017 Zhou
9,783,456 B1 10/2017 Zhou
10,098,834 B2 10/2018 Zhou
10,112,983 B2 10/2018 Zhou
10,441,633 B2 10/2019 Zhou
10,561,709 B2 2/2020 Zhou
2004/0126860 A1 7/2004 Epstein et al.
2005/0214823 A1 9/2005 Blume et al.
2006/0019888 A1 1/2006 Zhou
2006/0160062 A1 7/2006 Young
2006/0194734 A1 8/2006 Zhou
2006/0199767 A1 9/2006 Zhou
2007/0083334 A1 4/2007 Mintz et al.
2007/0129296 A1 6/2007 Zhou
2007/0141548 A1 6/2007 Kohl et al.
2007/0190127 A1 8/2007 Zhou
2007/0213264 A1 9/2007 Zhou
2008/0039434 A1 2/2008 Colli
2008/0260713 A1 10/2008 Zhou
2009/0156488 A1 6/2009 Zhou
2009/0203595 A1 8/2009 Zhou
2010/0143317 A1 6/2010 Pecora
2011/0135595 A1 6/2011 Zhou
2011/0229444 A1 9/2011 Zhou
2011/0236477 A1 9/2011 Schneider et al.
2013/0078235 A1 3/2013 Zhou
2013/0079281 A1 3/2013 Zhou
2013/0143845 A1 6/2013 Supple et al.
2013/0196911 A1 8/2013 Jay et al.
2013/0259924 A1 10/2013 Bancel et al.
2014/0031284 A1 1/2014 Zhou
2014/0135265 A1 5/2014 Zhou
2014/0364366 A1 12/2014 Zhou
2015/0284440 A1 10/2015 Zhou
2016/0089329 A1 3/2016 Zhou
2016/0095903 A1 4/2016 Zhou
2016/0152727 A1 6/2016 Zhou
2016/0297859 A1 10/2016 Zhou
2016/0324876 A1 11/2016 Zhou
2017/0007671 A1 1/2017 Zhou
2017/0189489 A1 7/2017 Zhou
2017/0232068 A1 8/2017 Zhou
2017/0313784 A1 11/2017 Zhou
2017/0326204 A1 11/2017 Zhou
2017/0360889 A1 12/2017 Zhou
2017/0368140 A1 12/2017 Zhou
2018/0104311 A1 4/2018 Zhou
2018/0133291 A1 5/2018 Zhou
2019/0240145 A1 8/2019 Zhou

FOREIGN PATENT DOCUMENTS

CN 1138785 C 2/2004
CN 1498656 A 5/2004
CN 1655804 A 8/2005
CN 1715926 A 1/2006
CN 1743005 A 3/2006
CN 1743006 A 3/2006
CN 1768859 A 5/2006
CN 1836731 A 9/2006
CN 101007027 A 8/2007
CN 101310766 A 11/2008
CN 101310779 A 11/2008
CN 101394861 A 3/2009
CN 101636656 A 1/2010
CN 102159236 A 8/2011
CN 102231987 A 11/2011
CN 102470161 A 5/2012
CN 103857695 A 6/2014
CN 104337813 A 2/2015
DE 3218121 A1 11/1983
EP 0 036 676 A1 9/1981
EP 0 052 322 A2 5/1982
EP 0 058 481 A1 8/1982
EP 0 088 046 A2 9/1983
EP 0 102 324 A2 3/1984
EP 0 143 949 A1 6/1985
EP 0 647 449 A1 6/1985
EP 0 133 988 A2 3/1995
EP 0 142 641 A2 5/1995
EP 0 896 586 B1 10/2006
EP 1 731 910 A1 12/2006
EP 1 187 634 B1 12/2007
FR 2972328 A1 9/2012
JP S607934 A 1/1985
JP A 2005-500025 1/2005
RU 2180843 C2 3/2002
RU 2457854 C2 8/2012
WO WO 1989/001489 A 2/1989
WO WO 1990/011354 A1 10/1990
WO WO 1991/001140 A1 2/1991
WO WO 1992/0018627 10/1992
WO WO 1993/004169 A1 3/1993
WO WO 1994/000140 1/1994
WO WO 1994/026298 A1 11/1994
WO WO 1995/032724 12/1995
WO WO 1996/015812 5/1996
WO WO 1997/009425 A1 3/1997
WO WO 1998/048827 A1 11/1998
WO WO 1999/018976 A1 4/1999
WO WO 1999/049062 A1 9/1999
WO WO 2000/037095 A1 6/2000
WO WO 2000/064400 A2 11/2000
WO WO 2000/078347 A1 12/2000
WO WO 2001/064877 A2 9/2001
WO WO 2001/070307 A1 9/2001
WO WO 2001/089568 A1 11/2001
WO WO 2002/024889 A2 3/2002

(56) References Cited

FOREIGN PATENT DOCUMENTS

WO WO 2002/040683 A2 5/2002
WO WO 2002/048191 A2 6/2002
WO WO 2003/035095 A1 5/2003
WO WO 2003/099300 A1 12/2003
WO WO 2003/099320 A1 12/2003
WO WO 2003/099321 A1 12/2003
WO WO 2003/100046 A1 12/2003
WO WO 2004/030716 A2 4/2004
WO WO 2004/030717 A2 4/2004
WO WO 2004/050894 A2 6/2004
WO WO 2004/112763 A2 12/2004
WO WO 2005/018673 A1 3/2005
WO WO 2007/062594 A1 6/2007
WO WO 2007/076701 A1 7/2007
WO WO 2008/028405 A1 3/2008
WO WO 2008/089994 A1 7/2008
WO WO 2008/128161 A2 9/2008
WO WO 2009/033373 A1 3/2009
WO WO 2010/030317 A2 3/2010
WO WO 2010/060265 A1 6/2010
WO WO 2010/060266 A1 6/2010
WO WO 2010/142141 A1 12/2010
WO WO 2011/011388 A2 12/2010
WO WO 2011/091723 A1 8/2011
WO WO 2011/112791 A1 9/2011
WO WO 2011/112864 A1 9/2011
WO WO 2012/012682 A2 1/2012
WO WO 2013/053076 A1 4/2013
WO WO 2013/053158 A1 4/2013
WO WO 2013/053201 A1 4/2013
WO WO 2014/056121 A1 4/2014
WO WO 2014/138502 A1 9/2014
WO WO 2014/187342 A1 11/2014
WO WO 2015/010449 A1 1/2015
WO WO 2015/101182 A1 7/2015
WO WO 2015/101208 A1 7/2015
WO WO 2016/058493 A1 4/2016

OTHER PUBLICATIONS

Balligand et al., Cardiac endothelium and tissue growth, Prog. Cardiovasc. Dis., 39(4):351-360 (1997).

Bradley et al., "Limits of cooperativity in a structurally modular protein: response of the notch ankyrin domain to analogous alanine substitutions in each repeat," J. Mol. Mol., 324:373-386 (2002).

Britsch et al.., "The ErbB2 and ErbB3 receptors sand their ligand, neregulin-1, are essential for development of the sympathetic nervous system," Genes Dev., 12:1825-1836 (1998).

Buchwald et al., "Long-term, continuous intravenous heparin administration by an implantable infusion pump in ambulatory patients with recurrent venous thrombosis," Surgery, 88(4):507-516 (1980).

Buonanno et al., "Neuregulin and ErbB receptor signaling pathways in the nervous system," Curr. Opin. Neurobiol., 11:287-296 (2001).

Cameron, "Recent advances in transgenic technology" Mol. Biotech., 7:253-265 (1997).

Carraway et al., "Neuregulin-2, a new ligand of ErbB/ErbB4-receptor tyrosine kinase," Nature, 387:512-516 (1997).

Chan et al., 2008, "Identification of Cardiac-Specific Myosin Light Chain Kinase," Circ. Res., vol. 102:571-580.

Chang et al., "Ligands for ErbB-family receptors encoded by a neuregulin-like gene," Nature, 387:509-512 (1997).

Chen et al., "Expression and Regulation of Cardiotrophin-1 in Ischemia-1 Reinfusion Cardiac Muscle of Rats and Effect of Neuregulin-1," J. Appl. Clin. Pediatr., 21(1):29-52 (2006).

Chien et al., "Regulation of cardiac gene expression during myocardial growth and hypertrophy: molecular studies of an adaptive physiologic response," FASEB J., Dec. 1991; 5(15):3037-3046.

Chien, "Molecular advances in cardiovascular biology," Science, 260(5110):916-917 (1993).

Cohen et al., "Emerging technologies for sequencing antisense oligonucleotides: capillary electrophoresis and mass spectrometry," Adv. Chromatogr., 36:127-162 (1996).

Cole et al., Monoclonal Antibodies and Cancer Therapy, Alan R. Liss, Inc., pp. 77-96 (1985).

Colucci et al., "Pathphysiology of heart failure," Chapter 13 in Heart Diseases: A textbook of cardiovascular medicine, Braunwald, ed., Saunders, Philadelphia. 1996; 5:394-420.

Corfas et al., "Neuregulin 1-erbB signaling and the molecular/cellular basis of schizophrenia," Nature Neuroscience, 7(6):575-580 (2004).

Cote et al., "Generation of human monoclonal antibodies reactive with cellular antigens," Proc. Natl. Acad. Sci., U.S.A., 80(7):2026-2030 (1983).

Crone et al., "ErbB2 is essential in the prevention of dilated cardiomyopathy," Nat Med., 8(5):459-465 (2002).

Cronin et al., "Cystic fibrosis mutation detection by hybridization to light-generated DNA probe arrays," Hum. Mutat., 7(3):244-255 (1996).

Database Biosis, "Deficient cardiac neuregulin-ErbB signaling in type 2 diabetes, and beneficial effects of treatment with neuregulin-1," Database accession No. PREV201000179850, Nov. 2009 (2 pages).

Dias et al., "The molecular basis of skeletal muscle differentiation," Semin Diagn Pathol., Feb. 1994; 11(1):3-14.

Doggen et al., "Deficient cardiac neuregulin-ErbB signaling in type 2 diabetes, and beneficial effects of treatment with neuregulin-1," Circulation, 82nd Scientific Session of the American-Heart Association, Orlando, Florida, Nov. 13-18, 2009, 120(18, Suppl. 2):S828 (2009).

During et al., "Controlled release of dopamine from a polymeric brain implant: in vivo characterizaiton," Ann. Neurol., 25(4):351-356 (1989).

Eppstein et al., "Biological activity of liposome-encapsulated murine interferon gamma is mediated by a cell membrane receptor," Proc. Natl. Acad. Sci. U S A., Jun. 1985; 82(11):3688-3692.

Eum et al., "Necrosis and apoptosis: sequence of liver damage following reperfusion after 60 min ischemia in rats," Biochem. Biophys. Res. Comm., 358:500-505 (2007).

Falls et al., "Neuregulins: functions, forms, and signaling strategies," Exp. Cell Res., 284(1):14-30 (2003).

Fang et al., "Neuregulin-1 preconditioning protects the heart against ischemia/reperfusion injury through a PI3K/Akt-dependent mechanism," Chin. Med. J., 123:3597-3604 (2010).

Florini et al., "Stimulation of myogenic differentiation by a neuregulin, glial growth factor 2," J. Biol. Chem., 271(22):12699-12702 (1996).

Galindo et al., "Anti-remodeling and anti-fibrotic effects of the neuregulin-1β glial growth factor 2 in a large animal model of heart failure," J. Am. Heart Assoc.,3(5):e000773 (2014).

Galindo et al., "Neuregulin as a heart failure therapy and mediator of reverse remodeling," Curr. Heart Fail. Rep., 11(1):40-49 (2014).

Gao et al., "A Phase II, randomized, double-blind, multicenter, based on standard therapy, placebo-controlled study of the efficacy and safety of recombinant human neuregulin-1 in patients with chronic heart failure," J. Am. Coll. Cardiol., 55(18):1907-1914 (2010).

Genbank Accession No. AJ247087, Apr. 15, 2005.

Genbank Accession No. BC_109097; GI:80478928, Nov. 4, 2005.

Genbank Accession No. NM_001110810, Nov. 24, 2007.

Gewirtz et al., "Nucleic acid therapeutics: state of the art and future prospects" Blood, 92(3):712-736 (1998).

Ginn et al., "Gene therapy clinical trials worldwide to 2012—an update," J. Gene Med., 15:65-77 (2013).

Goodson, in Medical Applications of Controlled Release, vol. 2, pp. 115-138 (1984).

Gray H., Gray's Anatomy: The Anatomical Basis of Medicine and Surgery, 1995, Ed. Williams et al., Churchill Livingstone, Edinburgh, pp. 264-254, 298-310 and 739-771.

Griffin et al., "DNA sequencing. Recent innovations and future trends," Appl. Biochem. Biotechnol., 38(1-2):147-159 (1993).

Gu et al., "Cardiac functional improvement in rats with myocardial infarction by up-regulating cardiac myosin light chain kinase with neuregulin," Cardiovasc. Res., 88(2):334-343 (2010).

Guo et al., "Neuroprotective effects of neuregulin-1 in rat models of focal cerebral ischemia," Brain Res., 1087:180-185, 2006.

(56) References Cited

OTHER PUBLICATIONS

Hein et al., "Altered expression of titin and contractile proteins in failing human myocardium," J. Mol. Cell Cardiol., 26(10):1291-1306 (1994).
Hervent et al., "Left ventricular diastolic dysfunction in obese diabetic mice is attenuated by pharmacological inhibition of dipeptidyl peptidase IV," Eur. J. Heart Failure Supplements, 12:S12-S16, Abstract 388, (2013).
Higashiyama et al., "A novel brain-derived member of the epidermal growth factor family that interacts with ErbB3 and ErbB4," J. Biochem., 122:675-680 (1997).
Hijazi et al., "NRG-3 in human breast cancers: activation of multiple erbB family proteins," Int. J. Oncol., 13:1061-1067 (1998).
Holmes et al., "Identification of heregulin, a specific activator of p185erbB2," Science, 256:1205-1210 (1992).
Huang et al., "Effects of neuregulin-1 on ventricular remolding in experimental diabetic cardiomyopathy," Chinese Pharmacological Bulletin, 27(11):1532-1536 (2011) (English abstract).
Huang, "Experimental study of the NRG-1 treatment in diabetic cardiomyopathy rats," Chinese Master's Theses Full-text Database Medicine and Health Sciences, Feb. 2, 2012, No. 4, E065-60 (English abstract).
Hwang et al., "Hepatic uptake and degradation of unilamellar sphingomyelin/cholesterol liposomes: a kinetic study," Proc. Natl. Acad. Sci. U S A., Jul. 1980; 77(7):4030-4034.
International Search Report for International Application No. PCT/CN2006/03694, dated Apr. 12, 2007.
International Search Report for International Application No. PCT/AU99/01137, Mar. 10, 2000.
International Search Report for International Application No. PCT/CN03/00355, dated Jul. 3, 2003.
Izumo et al., "Calcineurin—the missing link in cardiac hypertrophy," Nat. Med., 4(6):661-662 (1998).
Jabbour et al., "Parenteral administration of recombinant human neuregulin-1 to patients with stable chronic heart failure produces favourable acute and chronic haemodynamic responses," Eur. J. Heart Fail., 13(1):83-92 (2011).
Joliot et al., "Antennapedia homebox peptide regulates neural morphogenesis," Proc. Natl. Acad. Sci., U.S.A., 88(5):1864-1868 (1991).
Jones et al., "Binding interaction of the heregulinbeta egf domain with ErbB3 and ErbB4 receptors assessed by alanine scanning mutagenesis," J. Biol. Chem.,273(19):11667-11674 (1998).
Kida et al., "Congestive heart failure in type 2 diabetes—clinical features, risk factors, characterization of cardiac function, and survival prognosis," J. Japan Diab. Soc., 44(11):887-894 (2001). English abstract attached.
Köhler et al., "Continuous cultures of fused cells antibody of predifined specificity," Nature, 256(5517):495-497 (1975).
Kozbor et al., "The production of monoclonal antibodies from human lymphocytes," Immunol. Today, 4(3):72-79 (1983).
Kuramochi et al., "Cardiac endothelial cells regulate reactive oxygen species-induced cardiomyocyte apoptosis through neuregulin-1β/erbB4 signaling," J. Biol. Chem., 279(49):51141-51147 (2004).
Lakso et al., "Targeted oncogene activation by site-specific recombination in transgenic mice," Proc. Natl. Acad. Sci., U.S.A., 89(14):6232-6236 (1992).
Langer et al., "Biocompatibility of polymeric delivery systems for macromolecules," J. Biomed. Mater. Res., Mar. 1981; 15(2):267-277.
Langer et al., "Chemical and physical structure of polymers as carriers for controlled release of bioactive agents: a review," J. Macromol. Sci. Rev. Macromol. Chem. Phys., 23(1):61-126 (1983).
Langer, "Controlled release of macromolecules," Chemtech, 12:98-105 (1982).
Langer, "New methods of drug delivery," Science, 249(4976):1527-1533 (1990).
Levy et al., "Inhibition of calcification of bioprosthetic heart valves by local controlled-release disphosphonate," Science, 228(4696):190-192 (1985).
Li et al., "Targeted mutation of the DNA methyltransferase gene results in embryonic lethality," Cell, 69(6):915-926 (1992).
Li et al., "Therapeutic effects of neuregulin-1 in diabetic cardiomyopathy rats," Cardiovascular Diabetolgoy, 10(1):69, pp. 1-8 (2011).
Liu et al., "Effects of neuregulin on Rhesus monkey heart failure induced by rapid pacing," Sichuan Da Xue Xue Bao Yi Xue Ban, 2009, 40(1):93-96 (in Chinese with English Abstract).
Liu et al., "Neuregulin-1/ErbB-activation improves cardiac function and survival in models of ischemic, dilated, and viral cardiomyopathy," J. Am. Coll. Cardiol., 2006, 48(7):1438-1447.
Liu, "Protective effects of neuregulin-1β on chronic contractibility cardiac failure and correlative mechanisms research," Chinese Master's Thesis Full-text database, Medicine and Health Sciences, Jun. 2010, English abstract attached.
Luo et al., "Computational analysis of molecular basis of 1:1 interactions of NRG-1beta wild-type and variants with ErbB3 and ErbB4," Proteins, 59(4):742-756 (2005).
Macera et al., 1992, "Localization of the Gene Coding for Ventricular Myosin Regulatory Light Chain (MYL2) to Human Chromosome 12q23-q24.3," Genomics, vol. 13:829-831; Genbank Accession No. NM00432.
Mahar et al., "Subchronic peripheral neuregulin-1 increases ventral hippocampal neurogenesis and induces antidepressant-lik effects," PLoS One, 6(10):e26610 (2011).
Mahmood et al., "Selection of the first-time dose in humans: comparison of different approacheds based on interspecies scaling of clearance," J. Clin. Pharm., 43:692-697 (2003).
Massova et al., "Computational alanine scanning to probe protein-protein interactions: a novel approach to evaluate binding fee energies," J. Am. Chem. Soc., 121(36):8133-8143 (1999).
Maxam et al., "A new method for sequencing DNA," Proc. Natl. Acad. Sci., U.S.A., 74(2):560-564 (1977).
MeSH entry for Neuregulin-1, retrieved online from http:www.ncbi.nlm.nih.gov/mesh/68020890, entry dated 2000. Retrieved on Jul. 28, 2021.
Montoliu, "Gene transfer strategies in animal transgenesis" Cloning and Stem Cells, 4(1):39-46 (2002).
Morrison et al., "Chimeric human antibody molecules: mouse antigen-binding domains with human constant region domains," Proc. Natl. Acad. Sci., U.S.A., 81(21):6851-6855 (1984).
Naeve et al., "Accuracy of automated DNA sequencing: a multi-laboratory comparison of sequencing results," Biotechniques, 19(3):448-453 (1995).
Neuberger et al., "Recombinant antibodies possessing novel effector funtions," Nature, 312(5995):604-608 (1984).
Ngo et al., "Computational complexity, protein structure prediction, and the Levinthal paradox," In Merz and Le Grand (Eds.), The Protein Folding Problem and Tertiary Structure Prediction. Birkhauser:Boston, pp. 491-495 (1994).
Niemann, "Transgenic fam animals get off the ground" Transgenic Res., 7:73-75 (1998).
Notice of Allowability mailed Apr. 16, 2010 in U.S. Appl. No. 10/997,167.
Office Action mailed Apr. 29, 2010, in U.S. Appl. No. 11/429,203.
Office Action mailed Dec. 22, 2008 in U.S. Appl. No. 10/997,167.
Office Action mailed Dec. 13, 2007, in U.S. Appl. No. 11/429,203.
Office Action mailed Feb. 22, 2010, in U.S. Appl. No. 11/429,202.
Office Action mailed Feb. 4, 2009, in U.S. Appl. No. 11/429,203.
Office Action mailed Jan. 16, 2007, in U.S. Appl. No. 11/429,202.
Office Action mailed Jan. 3, 2008, in U.S. Appl. No. 11/429,202.
Office Action mailed Jun. 26, 2009 in U.S. Appl. No. 10/997,167.
Office Action mailed Jun. 27, 2008, in U.S. Appl. No. 11/429,203.
Office Action mailed Mar. 7, 2008 in U.S. Appl. No. 10/997,167.
Office Action mailed May 5, 2009, in U.S. Appl. No. 11/429,202.
Office Action mailed Nov. 9, 2009 in U.S. Appl. No. 10/997,167.
Office Action mailed Sep. 17, 2009, in U.S. Appl. No. 11/429,203.
O'Gorman et al., "Recombinase-mediated gene activation and site-specific integration in mammalian cells," Science, 251(4999):1351-1355 (1991).
Olson et al., "Regulation of muscle transcription by the MyoD family. The heart of the matter," Circ. Res., 1993, 72(1):1-6.

(56) References Cited

OTHER PUBLICATIONS

Parker et al., "p53-independent expression of p21Cipl in muscle and other terminally differentiating cells," Science, 267(5200):1024-1027 (1995).
Partial European Search Report for European Application No. 08020020.7, Jan. 7, 2009.
PCT International Search Report dated Nov. 29, 2007, in International Application No. PCT/CN2007/002531, filed Aug. 21, 2007.
Pentassuglia et al., "The Role of Neuregulin 1β/ErbB signaling in the heart," Exp. Cell Res., 315:627-637 (2009).
Physicians' Desk Reference. Medical Economics Data Production Co., Montvale, NJ. 1994; pp. 2314-2320.
Polak et al., 1991, "A Novel Calmodulin Antagonist, CGS 9343B, Modulates Calcium-Dependent Changes in Neurite Outgrowth and Growth Cone Movements," J. Neurosci., vol. 11(2):534-542.
Prelle et al., "Establishment of pluripotent cell lines from vertebrate species—present status and future prospects" Cells Tissues Organs, 165:220-236 (1999).
Ramachandran et al., Vet. Pathol., 45:698-706 (2008).
Ristevski, "Making better transgenic models" Mol. Biotech., 29:153-163 (2005).
Rumyantsev, "Interrelations of the proliferation and differentiation processes during cardiac myogenesis and regeneration," Int. Rev. Cytol., 51:186-273 (1977). (2 parts).
Sadick et al., "Analysis of heregulin-induced ErbB2 phosphorylation with a high-throughput Kinase receptor activation enzyme-linked immunosorbant assay," Anal. Biochem., 235:207-214 (1996).
Saiki et al., "Analysis of enzymatically amplified beta-globin and HLA-DQα DNA with allele-specific oligonucleotide probes," Nature, 324(6093):163-166 (1986).
Saiki et al., "Genetic analysis of amplified DNA with immobilized sequence-specific oligonucleotide probes," Proc. Natl. Acad. Sci. U.S.A., 86(16):6230-6234 (1989).
Sanger et al., "dna sequencing with chain-terminating inhibitors," Proc. Natl. Acad. Sci., U.S.A., 74(12):5463-5467 (1977).
Sawyer et al., "Modulation of anthracycline-induced myofibrillar disarray in rat ventricular myocytes by neuregulin-1beta and anti-erbB2: potential mechanism for trastuzumab-induced cardiotoxicity," Circulation, 105(13):1551-1554 (2002).
Schaper et al., "Impairment of the myocardial ultrastructure and changes of the cytoskeleton in dilated cardiomyopathy," Circulation, 83(2):504-514 (1991).
Sefton, "Implantable pumps," Crit. Rev. Biomed. Eng., 14(3):201-240 (1987).
Seguchi et al., 2007, "A Cardiac Myosin Light Chain Kinase Regulates Sarcomere Assembly in the Vertebrate Heart," The Journal of Clinical Investigation, vol. 117(10):2812-2824.
Sharma et al., 1979, "Preparation and Assay of the Ca2+-Dependent Mudulator Protein," Adv. Cyclic Nucleotide Res., vol. 10:187-198.
Shyu et al., Neurobio. Aging, vol. 25, pp. 935-944 (2004).
Sidman et al., "Controlled release of macromolecules and pharmaceuticals from synthetic polypeptides based on glutamic acid," Biopolymers, Jan. 1983; 22(1):547-556.
Sigma Genosys, "Designing custom peptides," retrieved from URL: http://www.sigma-genosys.com/peptide_design.asp>, retrieved on Dec. 16, 2004, pp. 1-2.
Simpson et al., "Myocyte hypertrophy in neonatal rat heart cultures and its regulation by serum and by catecholamines," Circ. Res. 51(6):787-801 (1982).
Slamon et al., "Use of chemotherapy plus a monoclonal antibody against HER2 for metastatic breast cancer that overexpresses HER2," N. Engl. J. Med., 344(11):783-792 (2001).
Smith, "Gene transfer in higher animals: theoretical considerations and key concepts" J. Biotechnol., 99:1-22 (2002).
Sobey et al., "Allopurinol and amlodipine improve coronary vasodilatation after myocardial ischaemia and reperfusion in anaesthetized dogs," Br. J. Pharmacol., 108:342-347 (1993).
Stevenson et al., "Optimizing therapy for complex or refractory heart failure: a management algorithm," Am. Heart J., 135(6 Pt 2 Su):S293-S309 (1998).
Swynghedauw, "Molecular mechanisms of myocardial remodeling," Physiol. Rev., 79(1):215-262 (1999).
Takemura, Nihon Kyobu Geka Gakkai, pp. 247-253, 1993 (Abstract Only).
The Fantom Consrtium et al., "The transcriptional landscape of the mammalian genome," Science, 309:1559-1563 (2005).
Thomas et al., "Site-directed mutagenesis by gene targeting in mouse embryo-derived stem cells," Cell, 51(3):503-512 (1987).
Tsutamoto, "BNP and NT-proBNP as a cardio-renal biomark," Igaku No Ayumi, 232(5):459-465 (2010). English abstract attached.
U.S. Department of Health and Human Services, Food and Drug Administration, Center for Drug Evaluation and Research (CDER), "Guidance for Industry, estimating the maximum safe starting dose in initial clinical trials for therapeutics in adult heathy volunteers," Jul. 2005.
Voet and Voet, Biochemistry, 2nd edition, John Wiley & Sons, Inc., pp. 235-241 (1995).
Wallace et al., 1983, "Assay of Calmodulin by Ca2 -Dependent Phosphodiesterase," Methods Enzymol, vol. 102:39-47.
Wang et al., "Improvement of cardiac function and reversal of gap junction remodeling by Neuregulin-1β in volume-overloaded rats with heart failure," J. Geriatr. Cardiol., 9(2):172-179 (2012).
Watson et al., Molecular Biology of the Gene, 4th Edition, The Bejacmin/Cummings Publishing Company, Inc., Menlo Park, CA, p. 224 (1987).
Wells, "Additivity of mutational effects in proteins," Biochem., 29(37):8509-8517 (1990).
Wilmut et al., "Viable offspring derived from fetal and adult mammalian cells," Nature, 385(6619):810-813 (1997).
Yarden et al., "Untangling the ErbB signaling network," Nat. Rev. Mol. Cell Biol., 2(2):127-137 (2001).
Yellon et al., "Myocardial Reperfusion Injury" N. Engl. J. Med., 357:1121-1135 (2007).
Zhao et al., "Selective disruption of neuregulin-1 function in vertebrate embryos using ribozyme-tRNA transgenes," Development, May 1998; 125(10):1899-1907.
Zhao et al., "Neuregulins promote survival and growth of cardiac myocytes. Persistence of ErbB2 and ErbB4 expression in neonatal and adult ventricular myocytes," J. Biol. Chem., 273(17):10261-10269 (1998).
Zhou et al., "Retinoid-dependent pathways suppress myocardial cell hypertrophy," Proc. Natl. Acad. Sci. U S A., Aug. 1, 1995; 92(16):7391-7395.
Wikipedia entry for "Cardiomyopathy," retrieved from the internet, available as early as Jan. 2021 : <URL: http://en.wikipedia.org/wiki/Cardiomyopathy>.

SEQUENCE LISTING

```
Sequence total quantity: 2
SEQ ID NO: 1            moltype = AA  length = 61
FEATURE                 Location/Qualifiers
source                  1..61
                        mol_type = protein
                        organism = Homo sapiens
SEQUENCE: 1
SHLVKCAEKE KTFCVNGGEC FMVKDLSNPS RYLCKCPNEF TGDRCQNYVM ASFYKAEELY  60
Q                                                                  61

SEQ ID NO: 2            moltype = AA  length = 23
FEATURE                 Location/Qualifiers
source                  1..23
                        mol_type = protein
                        organism = Homo sapiens
SEQUENCE: 2
AEKEKTFCVN GGECFMVKDL SNP                                          23
```

COMPOSITIONS AND METHODS FOR TREATING HEART FAILURE

This application is a divisional application of U.S. patent application Ser. No. 14/350,050, filed Apr. 4, 2014, which is a U.S. national stage application of PCT/CN2012/001354, having an international filing date of Oct. 8, 2012, which claims priority to PCT/CN2011/001691, having an international filing date of Oct. 10, 2011, and to PCT/CN2011/081699, having an international filing date of Nov. 2, 2011, each of which is incorporated herein by reference in its entirety and for all purposes.

The instant application contains a Sequence Listing which has been submitted electronically in ASCII format and is hereby incorporated by reference in its entirety. Said ASCII copy, created on Jun. 23, 2014, is named 11748-045-999_SL.txt and is 1,221 bytes in size.

1. FIELD OF THE INVENTION

The present invention relates to the use of neuregulin protein for the preparation of medication for preventing, treating or delaying heart failure in humans and methods for preventing, treating or delaying heart failure in humans using said medication. Particularly, the present invention provides methods for preventing, treating or delaying heart failure using the medication comprising a neuregulin protein in specific populations of chronic heart failure patients.

2. BACKGROUND OF THE INVENTION

Heart failure affects approximately five million Americans, and more than 550,000 new patients are diagnosed with the condition each year. Current drug therapy for heart failure is primarily directed to angiotensin-converting enzyme (ACE) inhibitors, which are vasodilators that cause blood vessels to expand, lowering blood pressure and reducing the heart's workload. While the percent reduction in mortality has been significant, the actual reduction in mortality with ACE inhibitors has averaged only 3%-4%, and there are several potential side effects. Additional limitations are associated with other options for preventing or treating heart failure. For example, heart transplantation is clearly more expensive and invasive than drug treatment, and it is further limited by the availability of donor hearts. Uses of mechanical devices, such as biventricular pacemakers, are similarly invasive and expensive. Thus, there has been a need for new therapies given the deficiencies in current therapies.

One promising new therapy involves administration of neuregulin (hereinafter referred to as "NRG") to a patient suffering from or at risk of developing heart failure. NRGs, a family of EGF-like growth factors, comprises a family of structurally related growth and differentiation factors that include NRG1, NRG2, NRG3 and NRG4 and isoforms thereof, are involved in an array of biological responses: stimulation of breast cancer cell differentiation and secretion of milk proteins; induction of neural crest cell differentiation to Schwann cells; stimulation of skeletal muscle cell synthesis of acetylcholine receptors; and, promotion of myocardial cell survival and DNA synthesis. In vivo studies of neuregulin gene-targeted homozygous mouse embryos with severe defects in ventricular trabecular formation and dorsal root ganglia development indicate that neuregulin is essential for heart and neural development.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmembrane kinase domain and cytoplasmic tyrosine kinase domain. After NRG bind to the extracellular domain of ErbB3 or ErbB4, it induces a conformational change that leads to heterodimer formation between ErbB3, ErbB4 and ErbB2 or homodimer formation between ErbB4 itself, which results in phosphorylation of the receptor's C-terminal domain inside the cell membrane. The phosphorylated intracellular domain then binds additional signal proteins inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart.

It has been shown that the EGF-like domains of NRG-1, ranging in size from 50 to 64-amino acids, are sufficient to bind to and activate these receptors. Previous studies have shown that neuregulin-1β (NRG-1B) can bind directly to ErbB3 and ErbB4 with high affinity. The orphan receptor, ErbB2, can form heterdimer with ErbB3 and ErbB4 with higher affinity than ErbB3 or ErbB4 homodimers. Research in neural development has indicated that the formation of the sympathetic nervous system requires an intact NRG-1B, ErbB2 and ErbB3 signaling system. Targeted disruption of the NRG-1β or ErbB2 or ErbB4 led to embryonic lethality due to cardiac development defects. Recent studies also highlighted the roles of NRG-1B, ErbB2 and ErbB4 in the cardiovascular development as well as in the maintenance of adult normal heart function. NRG-1β has been shown to enhance sarcomere organization in adult cardiomyocytes. The administration of a recombinant NRG-1β EGF-like domain significantly improves or protects against deterioration in myocardial performance in distinct animal models of heart failure as well as in clinical trials. These results make NRG-1 promising as a lead compound for the treatment of heart failure. However, there is still a need for more evidences of whether NRG-1 treatment can provide long-term benefits to the heart failure patients and whether the benefits can be provided to all chronic heart failure patients or some subpopulations.

3. SUMMARY OF THE INVENTION

In human clinical trials of neuregulin for treating heart failure, applicant discovered that evaluating New York Heart Association (NYHA) heart function classification or measuring plasma level of NT-proBNP or BNP in patients allows the selection of heart failure patients who will receive significant treatment benefits from neuregulin. Such benefits include significant reduction in mortality rate.

It has been discovered by applicant that NRG enhances cardiac muscle cell differentiation and organization of sarcomeric and cytoskeleton structure, as well as cell adhesion. It has been also discovered by applicant that that NRG significantly improves or protects against deterioration in myocardial performance in distinct animal models of heart failure and in clinical trials. Neuregulin, neuregulin polypeptide, neuregulin derivatives, or compounds which mimic the activities of neuregulins, fall within the scope of the present invention.

Thus, in a first aspect of the invention, a pharmaceutical composition comprise an effective amount of neuregulin is provided for treating chronic heart failure patients, and the patients received significant benefits from the pharmaceutical composition. In some embodiments, the benefit is significant reduction of mortality rate. In some embodiments, the benefit is significant reduction of rehospitalization. In some embodiments, the benefit is the improvement of the biomarkers levels which indicate the improvement of chronic heart failure. In some embodiments, the pharmaceutical composition is administered to the patients for an introduction regimen. In some optimized embodiments, the introduction regimen includes an administration of the pharmaceutical composition for at least consecutive 3, 5, 7 or 10 days. In some optimized embodiments, the pharmaceutical composition is administered to the patients for a maintenance regimen for at least 3, 6 or 12 months after the introduction regimen. In some optimized embodiments, the maintenance regimen includes administration of the pharmaceutical composition every 3, 5, 7 or 10 days.

In a second aspect, the invention provides a method to improve survival or reduce mortality of chronic heart failure patients, comprising administering a pharmaceutical composition comprising an effective amount of neuregulin to the chronic heart failure patients. In some embodiments, the pharmaceutical composition is administered to the patients for an introduction regimen. In some optimized embodiments, the introduction regimen includes administration of the pharmaceutical composition for at least consecutive 3, 5, 7 or 10 days. In some optimized embodiments, the pharmaceutical composition is administered to the patients for a maintenance regimen for at least 3, 6 or 12 months after the introduction regimen. In some optimized embodiments, the maintenance regimen includes an administration of the pharmaceutical composition every 3, 5, 7 or 10 days.

In a third aspect of the invention, a pharmaceutically effective amount of neuregulin is used for treating chronic heart failure patients whose plasma level of NT-proBNP is within a favorite treatment zone prior to neuregulin treatment. In one embodiment, the favorite treatment zone is no more than 4000 fmol/ml. In another embodiment, the favorite treatment zone is between 1600 fmol/ml and 4000 fmol/ml. In yet another embodiment, the favorite treatment zone is no more than 1600 fmol/ml. In another preferred embodiment, the plasma level is measured by immunoassay.

In a fourth aspect of the invention, a pharmaceutically effective amount of neuregulin is used for treating chronic heart failure patients who has a specific class of heart function classified by NYHA heart function classification. In some embodiments, the specific class of heart function is NYHA class II. In some embodiments, the specific class of heart function is NYHA class III.

In a fifth aspect, the invention features a method of selecting a heart failure patient for treatment by neuregulin. This method comprises measuring the plasma level of NT-proBNP in the patient. In one embodiment, a level of no more than 4000 fmol/ml is indicative of the patient being suitable for heart failure treatment by neuregulin. In another embodiment, a level of between 1600 fmol/ml and 4000 fmol/ml is indicative of the patient being suitable for heart failure treatment by neuregulin. In yet another embodiment, a level of no more than 1600 fmol/ml is indicative of the patient being suitable for heart failure treatment by neuregulin.

In a sixth aspect, the invention features a method of selecting a heart failure patient for treatment by neuregulin. This method comprises evaluating heart function class by NYHA heart function classification. In one embodiment, NYHA class II is indicative of the patient being suitable for heart failure treatment by neuregulin. In another embodiment, NYHA class III is indicative of the patient being suitable for heart failure treatment by neuregulin.

In a seventh aspect, the invention features a diagnostic kits for selecting a heart failure patient for treatment by neuregulin. In one embodiment, the diagnostic kits comprises immunoassay reagents to measure plasma level of NT-proBNP in a heart failure patient wherein a level of no more than 4000 fmol/ml is indicative of the patient being suitable for heart failure treatment by neuregulin. In another embodiment, a level of between 1600 fmol/ml and 4000 fmol/ml is indicative of the patient being suitable for heart failure treatment by neuregulin. In yet another embodiment, a level of no more than 1600 fmol/ml is indicative of the patient being suitable for heart failure treatment by neuregulin.

In a eighth aspect of the invention, the use of neuregulin protein for preparation of a medication was provided. The medication can be provided to chronic heart failure patients for long-term benefits. In one embodiment, the long-term benefit is the improvement of survival. In one embodiment, the long-term benefit is the reduction of re-hospitalization. In another embodiment, the long-term benefit is the improvement of biomarkers which indicate the long-term prognosis of chronic heart failure. In some embodiments, the medication is administered to the patients for an introduction regimen. In some optimized embodiments, the introduction regimen includes administration of medication for at least consecutive 3, 5, 7 or 10 days. In some optimized embodiments, the medication is administered to the patients for a maintenance regimen for at least 3, 6 or 12 months after the introduction regimen. In some optimized embodiments, the maintenance regimen includes an administration of the medication every 3, 5, 7 or 10 days.

In a ninth aspect of the invention, a companion diagnostic test was provided for the treatment of chronic heart failure by neuregulin protein. N-terminal pro-brain natriuretic peptide (NT-proBNP) is used as a biomarker for the companion diagnostic test. In one embodiment, a level of no more than 4000 fmol/ml is indicative of the patient being suitable for heart failure treatment by neuregulin. In another embodiment, a level of between 1600 fmol/ml and 4000 fmol/ml is indicative of the patient being suitable for heart failure treatment by neuregulin. In yet another embodiment, a level of no more than 1600 fmol/ml is indicative of the patient being suitable for heart failure treatment by neuregulin.

In a tenth aspect of the invention, a method of treating chronic heart failure using neuregulin is provided. The method comprises an evaluation procedure before treatment and decides whether each patient is suitable to receive neuregulin treatment according to the result of the evaluation. In one embodiment, the evaluation procedure includes NYHA heart function classification of a chronic heart failure patient. In another embodiment, the evaluation procedure includes test of plasma NT-proBNP or BNP for each chronic heart failure patient.

In a eleventh aspect of the invention, a companion diagnostic kit for deciding whether a chronic heart failure patient is suitable for receiving neuregulin protein treatment is provided. The companion diagnostic kit comprises a test kit for plasma NT-proBNP or BNP and an instruction of how to use the kit and how to judge whether the subject is suitable for neuregulin protein treatment according to the test result.

4. DETAILED DESCRIPTION OF THE INVENTION

For clarity of disclosure, and not by way of limitation, the detailed description of the invention hereinafter is divided into the subsections that follow. All publications mentioned herein are incorporated by reference to disclose and describe the methods and/or materials in connection with which the publications are cited.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "neuregulin" or "NRG" used in the present invention refers to proteins or peptides that can bind and activate ErbB2, ErbB3, ErbB4 or combinations thereof, including but not limited to all neuregulin isoforms, neuregulin EGF-like domain alone, polypeptides comprising neuregulin EGF-like domain, neuregulin mutants or derivatives, and any kind of neuregulin-like gene products that also activate the above receptors as described in detail below. Neuregulin also includes NRG-1, NRG-2, NRG-3 and NRG-4 proteins, peptides, fragments and compounds that mimic the activities of neuregulin. Neuregulin used in the present invention can activate the above ErbB receptors and modulate their biological reactions, e.g., stimulate acetylcholine receptor synthesis in skeletal muscle cell; and/or improve cardiocyte differentiation, survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4th Edition, 1987, The Bejacmin/Cummings Pub.co.,p.224). In preferred embodiments, neuregulin used in the present invention binds to and activates ErbB2/ErbB4 or ErbB2/ErbB3 heterodimers, for example, but not for the purpose of restriction, peptides including the 177-237 residues of NRG-1 β2 isoform containing the amino acid sequence: SHLVKCAEKEKTFCVNGGECF MVKDLSNPSRYLCKCPNEFTGDRCQNYVMASFYKAEELYQ (SEQ ID NO:1). The peptides including the 177-237 residues of NRG-1 β2 isoform comprises the EGF-like domain, which has been proved to be sufficient to bind to and activate the receptors.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256: 1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387:512-516 (1997); Higashiyama et al., J. Biochem., 122: 675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro (SEQ ID NO: 2), as described in U.S. Pat. No. 5,834,229.

The formulation, dosage and route of administration of a neuregulin protein, preferably in the form of pharmaceutical compositions, can be determined according to the methods known in the art (see e.g., Remington: The Science and Practice of Pharmacy, Alfonso R. Gennaro (Editor) Mack Publishing Company, April 1997; Therapeutic Peptides and Proteins: Formulation, Processing, and Delivery Systems, Banga, 1999; and Pharmaceutical Formulation Development of Peptides and Proteins, Hovgaard and Frkjr (Ed.), Taylor & Francis, Inc., 2000; Medical Applications of Liposomes, Lasic and Papahadjopoulos (Ed.), Elsevier Science, 1998; Textbook of Gene Therapy, Jain, Hogrefe & Huber Publishers, 1998; Adenoviruses: Basic Biology to Gene Therapy, Vol. 15, Seth, Landes Bioscience, 1999; Biopharmaceutical Drug Design and Development, Wu-Pong and Rojanasakul (Ed.), Humana Press, 1999; Therapeutic Angiogenesis: From Basic Science to the Clinic, Vol. 28, Dole et al. (Ed.), Springer-Verlag New York, 1999).

The neuregulin protein, can be formulated for oral, rectal, topical, inhalational, buccal (e.g., sublingual), parenteral (e.g., subcutaneous, intramuscular, intradermal, or intravenous), transdermal administration or any other suitable route of administration. The most suitable route in any given case will depend on the nature and severity of the condition being treated and on the nature of the particular neuregulin protein, which is being used. The neuregulin protein can be administered alone. Alternatively and preferably, the neuregulin protein is co-administered with a pharmaceutically acceptable carrier or excipient. Any suitable pharmaceutically acceptable carrier or excipient can be used in the present method (See e.g., Remington: The Science and Practice of Pharmacy, Alfonso R. Gennaro (Editor) Mack Publishing Company, April 1997).

According to the present invention, the neuregulin protein, alone or in combination with other agents, carriers or excipients, may be formulated for any suitable administration route, such as intracavernous injection, subcutaneous injection, intravenous injection, intramuscular injection, intradermal injection, oral or topical administration. The method may employ formulations for injectable administration in unit dosage form, in ampoules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogenfree water or other solvents, before use. Topical administration in the present invention may employ the use of a foam, gel, cream, ointment, transdermal patch, or paste.

Pharmaceutically acceptable compositions and methods for their administration that may be employed for use in this invention include, but are not limited to those described in U.S. Pat. Nos. 5,736,154; 6,197,801 B1; 5,741,511; 5,886,039; 5,941,868; 6,258,374 B1; and 5,686,102.

The magnitude of a therapeutic dose in the treatment or prevention will vary with the severity of the condition to be treated and the route of administration. The dose, and perhaps dose frequency, will also vary according to age, body weight, condition and response of the individual patient.

It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

Any suitable route of administration may be used. Dosage forms include tablets, troches, cachet, dispersions, suspensions, solutions, capsules, patches, and the like. See, Remington's Pharmaceutical Sciences. In practical use, the neuregulin protein, alone or in combination with other agents, may be combined as the active in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral. In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the neuregulin protein, alone or in combination with other agents to be administered may be administered in a vial of intravenous fluid, ranging from about 1 ml to 2000 ml. The volume of dilution fluid will vary according to the total dose administered.

The invention also provides for kits for carrying out the therapeutic regimens of the invention. Such kits comprise in one or more containers therapeutically effective amounts of the neuregulin protein, alone or in combination with other agents, in pharmaceutically acceptable form. Preferred pharmaceutical forms would be in combination with sterile saline, dextrose solution, or buffered solution, or other pharmaceutically acceptable sterile fluid. Alternatively, the composition may be lyophilized or desiccated; in this instance, the kit optionally further comprises in a container a pharmaceutically acceptable solution, preferably sterile, to reconstitute the complex to form a solution for injection purposes. Exemplary pharmaceutically acceptable solutions are saline and dextrose solution.

In another embodiment, a kit of the invention further comprises a needle or syringe, preferably packaged in sterile form, for injecting the composition, and/or a packaged alcohol pad. Instructions are optionally included for administration of composition by a physician or by the patient.

As used herein, "treat", "treatment" and "treating" refer to any manner in which the symptoms of a condition, disorder or disease are ameliorated or otherwise beneficially altered. The effect may be prophylactic in terms of completely or partially preventing a disease or symptom thereof and/or may be therapeutic in terms of a partial or complete cure for a disease and/or adverse effect attributable to the disease. Treatment also encompasses any pharmaceutical use of the compositions herein.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, viral, toxic or idiopathic forms. Chronic cardiac hypertrophy is a significantly diseased state which is a precursor to congestive heart failure and cardiac arrest.

As used herein, "protein" is synonymous with "polypeptide" or "peptide" unless the context clearly dictates otherwise.

As used herein, "plasma" is synonymous with "serum" unless the context clearly dictates otherwise.

As used herein, "long-term benefit" means benefit caused by a treatment or interference which may not be observed in a short period after the treatment or interference. For chronic heart failure patients, long-term benefit may be improvement of survival, reduction of re-hospitalization or improvement of biomarkers which indicate the long-term prognosis. In some embodiments, the time period for observation of the benefit is about 6 months. In some embodiments, the time period for observation of the benefit is about 1 year. In some embodiments, the time period for observation of the benefit is about 2 years. And in other embodiments, the time period for observation of the benefit is about 3 years, 5 years, 10 years or longer.

As used herein, "survival" means the time or probability one subject may remain alive or living. It could be expressed by survival time or survival rate. Survival time is the time period start from the diagnosis or treatment to the end of the life. Survival rate means the percentage of people who are alive for a given period of time after diagnosis or treatment. For each subject, prolonged survival time caused by a treatment or interference could be regarded as a benefit. For a group of subjects or large populations, prolonged mean survival time or increased survival rate could be regarded as a benefit.

As used herein, "re-hospitalization" means the times or frequency of the patient admitted to the hospital in a given period of time. The admission to the hospital may be caused by all conditions, or only caused by the same condition which is being treated. For each subject, a reduction of times of re-hospitalizations in a given period of time could be regarded as a benefit. And for a group of subjects or large populations, a reduction of total times or mean times of re-hospitalizations could be regarded as a benefit.

As used herein, "N-terminal brain natriuretic peptide" or "NT-proBNP" means the inactive remnant N-terminal proBNP, the latter is the pro hormone of BNP which is a hormonally active natriuretic peptide that is mainly released from the cardiomyocytes in the left ventricular wall. In reaction to stretch and tension of the myocardial wall the pro hormone proBNP splits into BNP and the hormonally inactive remnant NT-proBNP by proteolytic cleavage.

BNP and NT-proBNP plasma levels are promising tools in the daily management of suspected or established heart failure. Most studies on the use of BNP and NT-proBNP in clinical practice addressed their diagnostic properties, and an increasingly amount of evidence is available supporting the prognostic value of BNP and NT-proBNP. As NT-proBNP has about 6 times longer of half-life in the blood than BNP, it is more widely used as a diagnostic or prognostic marker for heart failure. The plasma NT-proBNP level can be analyzed by commercial kits. For the purpose of example, but not limitation, the commercial kits from Roche or Biomedica. In the examples of the present invention, the NT-proBNP level was detected by kit from Biomedica (Austria).

Both BNP and NT-proBNP levels in the blood are used for screening, diagnosis of heart failure and are useful to establish prognosis in heart failure, as both markers are typically higher in patients with worse outcome. And, it is discovered in the present invention that plasma level of BNP or NT-proBNP is indicative of the patient being suitable for heart failure treatment by neuregulin. In fact, any diagnostic or prognostic markers for heart failure can be used to determine whether a patient is suitable for heart failure treatment by neuregulin. The plasma level of NT-proBNP identified in this invention shall be used as guidance rather than a limitation for selection of heart failure patients who will receive significant treatment benefits from neuregulin. For example, using a plasma level of 5000 fmol/ml is still able to select heart failure patients who will receive treatment benefits from neuregulin, but some of these patients will receive treatment benefits in a lesser degree.

As used herein, "New York Heart Association" or "NYHA" heart function classification is a simple way of classifying the extent of heart failure. It places patients in one of four categories based on how much they are limited during physical activity; the limitations/symptoms are in regards to normal breathing and varying degrees in shortness of breath and/or angina pain: I, no symptoms and no limitation in ordinary physical activity, e.g. shortness of breath when walking, climbing stairs etc.; II, mild symptoms (mild shortness of breath and/or angina) and slight limitation during ordinary activity; III, marked limitation in activity due to symptoms, even during less-than-ordinary activity, e.g. walking short distances (20-100 m), comfortable only at rest; and IV, severe limitations, experiences symptoms even while at rest, mostly bedbound patients.

As used herein, "activity unit" or "EU" or "U" means the quantity of standard product that can induce 50% maximal reaction. In other words, to determine the activity unit for a given active agent, the EC50 must be measured. For example, if the EC50 for a batch of product was 0.1 μg, which would be one unit. Further, if lug of that product is being used, then 10 EU (I/O.1) is being used. The EC50 can be determined by any method known in the art, including the method employed by the inventors. This determination of the activity unit is important for quality control of genetically engineered products and clinically used drugs, permits product from different pharmaceuticals and/or different batch numbers to be quantified with uniform criteria.

The following is an exemplary, rapid, sensitive, high flux and quantitative method for determination of biological activity of NRG-1 through combining NRG with cell surface ErbB3/ErbB4 molecule and indirect mediation of ErbB2 phosphorylation (See e.g., Michael D. Sadick et al., 1996, Analytical Biochemistry, 235:207-214 and WO03/099300).

Briefly, the assay, termed a kinase receptor activation enzyme-linked immunosorbant assay (KIRA-ELISA), consists of two separate microtiter plates, one for cell culture, ligand stimulation, and cell lysis/receptor solubilization and the other plate for receptor capture and phosphotyrosine ELISA. The assay was developed for analysis of NRG-induced ErbB2 activation and utilizes the stimulation of intact receptor on the adherent breast carcinoma cell line, MCF-7. Membrane proteins are solubilized via Triton X-100 lysis and the receptor is captured in ELISA wells coated with ErbB2-specific antibodies with no cross-reaction to ErbB3 or ErbB4. The degree of receptor phosphorylation is then quantified by antiphosphotyrosine ELISA. A reproducible standard curve is generated with a EC50 of approximately 360 pM for heregulin beta 1 (177-244). When identical samples of HRG beta 1 (177-244) are analyzed by both the KIRA-ELISA and quantitative antiphosphotyrosine Western Blot analysis, the results correlate very closely with one another. The assay described in this report is able to specifically quantify tyrosine phosphorylation of ErbB2 that results from the interaction of HRG with ErbB3 and/or ErbB4.

Since most of the genetically engineered medicines are proteins and polypeptides, their activity can be determined by their amino acid sequences or the activity center formed by their spatial structure. Activity titer of protein and polypeptide is not consistent with their absolute quality, therefore cannot be determined with weight unit as that of chemical drugs. However, biological activity of genetically engineered medicines is generally consistent with their pharmacodynamics and titer determination system established through given biological activity can determine its titer unit. Therefore, biological activity determination can be part of a titration process of the substance with biological activity and is an important component of quality control of genetically engineered product. It is important to determine biological activity criteria for quality control of genetically engineered product and clinically used drugs.

Quantity of standard product that can induce 50% maximal reaction is defined as an activity unit (1 EU). Accordingly, product from different pharmaceuticals and of different batch numbers can be quantitated with uniform criteria.

B. EXAMPLES

Example 1: The Effect of Neucardin™ Administration by Different Routes on the Survival Rate of Rats with CHF

INTRODUCTION

In this study, we used a coronary artery ligation (CAL) induced CHF model to investigate whether administration of Neucardin™ by IV drip using a micro-injection pump or by subcutaneous (SC) bolus had any effects on survival rate and cardiac hemodynamics, 120 days after the initiation of administration of Neucardin™ 4 weeks after CAL. Echocardiography and cardiac remodeling were also used to determine cardiac function and recovery from CAL.

2. Methods:

2.1. Test animals:

Strain, Origin: Wistar rats, Shanghai SLAC Laboratory Animal CO. LTD; Weight, 200+10 g, male;

2.2 Test Article:

2.2.1 Neucardin™

Identification: Recombinant human neuregulin-1 for injection (rhNRG-1, Neucardin™)

Lot Number: 200607009

Manufacturer: Zensun (Shanghai) Sci & Tech Co., Ltd

Dose form: Lyophilized powder

Appearance: White or off-white cake

Labeled Content of rhNRG-1: 250 μg/vial

Specific activity: 4897 U/vial

Storage conditions: 2~8° C.

2.2.2 Vehicle:

Identification: Placebo for recombinant human neuregulin-1

Dose form: Lyophilized powder

Appearance: White or off-white cake

Composition: Human serum albumin, mannitol, phosphate, NaCl

Storage conditions: 2~8° C.

2.3 Procedure:

2.3.1 to Establish the Rat CHF Model:

The LAD of the rats was ligated. Briefly, the rats were anesthetized with ketamine hydrochloride (100 mg/kg, IP) and their chest was shaved and sterilized. The rats were endotracheally intubated and mechanically ventilated with room air (respiratory rate 60 breaths/min, tidal volume 20 ml). A left thoracotomy was then performed at the 4th and 5th intercostal space and then the skin was incised along the left sternal border. The fourth rib was then cut proximal to the sternum. The pericardial sac was perforated and the heart was exposed. The LAD was ligated approximately 2 mm from its origin using a 6-0 silk suture. Subsequently, the air within the thorax was removed and the chest was closed in three layers (ribs, muscles and then skin). The rats were then allowed to resume spontaneous respiration, recover from the anesthesia and were then returned to their cages. Rats were maintained during a period of 4 weeks, then echocardiography evaluated, included in the formal study if they were shown an EF % value of 30-45%. Animals from all Groups were housed 5 per cage, fed ad libitum with standard diet and had free access to pure water. Room temperature was maintained at 21+1° C. and in a12 h light/dark cycle.

2.3.2 IV Drip Via Microinjection Pump:

The method of IV drip of vehicle or Neucardin™ was through the tail vein. For this procedure, an appropriate rat restrainer was used according to the weight of the animal. The rat was placed near the restrainer and was gently placed into the apparatus. Normally the rats entered the restrainer without aid. Subsequently the tail of the rat was swabbed with a gauze dampened with alcohol to increase blood flow to the tail vein and to the intenerate skin corneum. The two lateral (on the side) tail veins were located and with the bevel of the needle facing upward with the needle almost parallel to the vein, the needle was inserted 2 mm into the tail vein 2-3 cm from the end of the tail. To confirm that the needle was successfully inserted into the tail vein, blood was extracted into the hub of the needle. The needle was fixed into the tail using medical tape. The infusion of drug or vehicle at the appropriate rate (0.2-0.4 ml/h) by microinjection pump or bolus injection was initiated.

2.3.3 SC Bolus

The SC bolus of vehicle or Neucardin™ was from the back of the rat. For this procedure, an appropriate rat restrainer was used according to the weight of the animal. The back of the rat was swabbed with gauze dampened with alcohol to sterilize the skin. With the bevel of the needle facing upward with the needle almost parallel to the skin, the needle was subcutaneously inserted 3-4 cm into the back of the rat. The needle was fixed onto the back using medical tape and connected to the perfusion tube. Then, the rat was placed near the restrainer and was gently placed into the apparatus. Normally the rats entered the restrainer with no aid. After fasten the restrainer, the bolus injection was initiated.

2.3.4 Experiment Groups and Drug Infusion:

MI rats were randomized by EF % value into four Groups as follows:

Group A (Negative control) for both IV and SC bolus. n=58 rats: IV drip of vehicle for 10-days by micro-injection pump at a speed of 0.2 ml/h for 8 h each day for the first 10 days, SC bolus of vehicle (same volume as Neucardin™), every 5 days until Day 120;

Group B (SC bolus Neucardin™), n=58: IV drip of vehicle by micro-injection pump at a speed of 0.2 ml/h for 8 h each day in the first 10 days, SC bolus Neucardin™ (10 μg/day), every 5 days until Day 120;

Group C (IV drip Neucardin™), n=57: IV drip of Neucardin™ (0.625 μg/kg/h) by micro-injection pump at a speed of 0.2 ml/h for 8 h each day for the first 10 days, SC bolus of vehicle (same volume as Neucardin™), every 5 days until Day 120.

Group D (IV drip and SC bolus Neucardin™), n=57: IV drip of Neucardin™ (0.625 μg/kg/h) by micro-injection pump at a rate of 0.2 ml/h for 8 h per day for the first 10 days, SC bolus of vehicle (same volume as Neucardin™) at 1st, 6th, 11th day, and then SC bolus Neucardin™ (10 μg/kg), every 5 days from 16th day to the end.

2.3.5 Data acquisition

Survival rate; Echocardiography parameters; Hemodynamics parameters;

3. Results 3.1 Survival rate:

Table 1 illustrates the survival rates between each Group. The survival rates were 48.3%, 62.1%, 64.9% and 82.5% in the IV drip & SC bolus of vehicle Group A, SC bolus of Neucardin™ Group B, IV drip of Neucardin™ Group C and IV drip & SC bolus of Neucardin™ Group D, respectively. All the survival rate or mean survival time of mortalities in Group B, C and D were improved or prolonged compared to Group A with Group D had best efficacy.

TABLE 1

Mortality, Survival rate and Mean survival time in the four Groups

| Group | Treatment | Start rat number | Deaths | Survival rat number | Survival rate (%) | Mean survival time of mortalities in days ± S.E. |
|---|---|---|---|---|---|---|
| A | Vehicle | 58 | 30 | 28 | 48.3% | 83.8 ± 5.9 |
| B | SC bolus Neucardin ™ | 58 | 22 | 36 | 62.1% | 91.4 ± 5.5 |
| C | IV drip Neucardin ™ | 57 | 20 | 37 | 64.9% | 97.5 ± 5.1 |
| D | SC bolus & IV drip Neucardin ™ | 57 | 10 | 47 | 82.5% | 107.5 ± 4.1 |

3.2 Echocardiography Parameters:

Echocardiography parameters were shown in Table 2. Four-weeks after coronary artery ligation and before administration of the test article, the CHF rats were randomized into four Groups according to their EF % values. As shown in Table 2, there were no significant differences between the four Groups before treatment (BT). 120 days after the start of administration, the EF % values were 30.7±3.1, 32.9 ±4.1, 33.5+3.4, 36.2±4.8% in the vehicle, Neucardin™ via SC bolus, Neucardin™ via IV drip and Neucardin™ via IV drip plus SC bolus Groups, respectively. After treatment, EF % and FS % of Group B, C and D were all higher than that of Group A.

TABLE 2

Echocardiography parameters in the four Groups

| Group | BT AT | N | LVEDd (cm) | LVEDs (cm) | EF % (%) | FS % (%) |
|---|---|---|---|---|---|---|
| A. Negative control | BT | 58 | 0.987 ± 0.083 | 0.829 ± 0.088 | 38.0 ± 5.5 | 16.2± |
| | AT | 25 | 1.100 ± 0.089 | 0.961 ± 0.090 | 30.7 ± 3.1 | 12.7± |
| B. SC bolus Neucardin ™ | BT | 58 | 0.992 ± 0.066 | 0.831 ± 0.066 | 38.2 ± 4.0 | 16.3± |
| | AT | 33 | 1.104 ± 0.063 | 0.952 ± 0.070 | 33.1 ± 4.1 | 13.9± |
| C. IV drip Neucardin ™ | BT | 57 | 0.985 ± 0.061 | 0.824 ± 0.068 | 38.5 ± 4.4 | 16.3± |
| | AT | 36 | 1.080 ± 0.072 | 0.929 ± 0.073 | 33.4 ± 3.4 | 14.0± |
| D. SC bolus & IV drip Neucardin ™ | BT | 57 | 0.979 ± 0.065 | 0.818 ± 0.066 | 38.7 ± 4.3 | 16.5± |
| | AT | 44 | 1.052 ± 0.087 | 0.893 ± 0.092 | 36.2 ± 4.8 | 15.3± |

BT: Before treatment;
AT: After treatment;

3.3 Hemodynamic Parameters:

Table 3 shows the MAP, HR, ±dp/dt, LVEDP and LVSP values as measured in the four Groups of anesthetized animals on day 121. When Neucardin™ was administered by SC bolus or by IV drip alone (Group B and C), Neucardin™ significantly increased dp/dt and −dp/dt by 19.6% and 27.1%, 22.5% and 29.8% compared to Group A. When Neucardin™ was administered by both IV drip and SC bolus routes (Group D), significant increases in mean arterial pressure (MAP, 112.3±5.5 mmHg), left ventricular systolic pressure (LVSP, 139.4±9.8 mmHg), ±dp/dt (7012.1+903.0 mmHg/s), −dp/dt (−4353.2±847.6 mmHg/s) compared to vehicle were obtained. Interestingly, these values of MAP, LVSP, ±dp/dt and −dp/dt were 10.6%, 9.2%, 38.5% and 37.8% higher than vehicle treated rats, respectively. The results showed that Group B, C and D were all better than Group A in hemodynamic parameters with Group D had best efficacy.

TABLE 3

Hemodynamics parameters in the four Groups

| Group | Treatment | N | SBP (mmHg) | DBP (mmHg) | MAP (mmHg) | LVSP (mmHg) |
|---|---|---|---|---|---|---|
| A | Vehicle | 14 | 118.7 ± 11.5 | 94.1 ± 12.3 | 102.3 ± 11.7 | 128.5 ± 14.7 |
| B | SC bolus Neucardin ™ | 27 | 123.8 ± 11.5 | 95.3 ± 8.9 | 104.9 ± 9.5 | 129.5 ± 13.6 |
| C | IV drip Neucardin ™ | 25 | 122.5 ± 10.5 | 95.0 ± 7.5 | 104.4 ± 8.2 | 131.7 ± 10.0 |
| D | SC bolus & IV drip Neucardin ™ | 35 | 132.6 ± 7.1 | 102.1 ± 5.3 | 112.3 ± 5.5 | 139.4 ± 9.8 |

| Group | Treatment | N | LVEDP (mmHg) | dp/dt (mmHg/s) | (−dp/dt) (mmHg/s) | Heart rate (Beat/min) |
|---|---|---|---|---|---|---|
| A | Vehicle | 14 | 5.8 ± 3.5 | 4995.6 ± 532.2 | 3087.5 ± 715.7 | 297.2 ± 16.0 |
| B | SC bolus Neucardin ™ | 27 | 4.5 ± 2.8 | 6050.9 ± 1231.3 | 4013.8 ± 838.3 | 292.6 ± 23.0 |
| C | IV drip Neucardin ™ | 25 | 4.0 ± 3.2 | 6199.9 ± 709.5 | 4098.9 ± 823.5 | 296.3 ± 13.5 |
| D | SC bolus & IV drip Neucardin ™ | 35 | 3.9 ± 2.5 | 7012.1 ± 903.0 | 4353.2 ± 847.6 | 292.5 ± 19.1 |

4. Conclusion

A combined administration of Neucardin™ by IV drip & SC bolus or administration of the peptide given by each route alone all increased the survival rate of rats with CHF induced by CAL and improved cardiac functional parameters compared to rats treated with vehicle.

Example 2: A Randomized, Double-Blinded, Multi-Center, Placebo Controlled Study to Evaluate the Efficacy and Safety of Recombinant Human Neuregulin 1 in Patients with Chronic Heart Failure Based on Standard Treatment To evaluate the efficacy of recombinant human neuregulin-1 for injection on chronic heart failure, a phase II, double-blinded, multi-center, placebo controlled, standard treatment based study was carried out in multiple clinical centers in China. A total of 195 patients with NYHA Class II or III stable chronic heart failure were enrolled and randomized into three groups: placebo, or 0.6 μg/kg and 1.2 μg/kg of rhNRG-1. There were no significant variations in demographics or background therapies among groups. According to the schedule, patients were administered the drug for 10 consecutive days in the hospital first, after finishing the day 11 follow up, they were discharged from the hospital. Another two on site follow up were at day 30 and day 90. A telephone interview was conducted one year after the last patient enrolled.

Investigational product:

Specification: Neucardin™, 61 amino acid polypeptide comprises the EGF-like domain of Neuregulin-1 β2 isoform, with the molecular weight of 7054 Dal (1 μg=0.14 nmol). 250 μg (5000 EU)/vial (lug=20 EU).

Preparation: For injection.

Mode of administration: Intravenously drip.

Storage: in safe place, with limited access and protected from light, at 3-8° C.

Placebo:

Specification: Excipient for Neucardin™ (250 μg/vial without active recombinant human neuregulin-1 protein).

Dosage groups:

| | Dosage | | |
|---|---|---|---|
| | 0 μg/kg/day | 0.6 μg/kg/day | 1.2 μg/kg/day |
| Administration | Intravenous infusion | | |
| Volume | 50 ml | | |
| Course | 10 hours per day, for consecutive 10 days | | |

Study Procedure

Criteria for participation in the trial included patients with CHF (NYHA class II or III) between the ages of 18 and 65 years old, LVEF≤40%, in relatively stable clinical condition (including clinical signs, symptoms and accepted standard treatment for CHF at the target dose or maximum tolerance dose for over 1 month). Major exclusion criteria included acute myocardial infarction, hypertrophic cardiomyopathy, constrictive pericarditis, significant valve disease or congenital heart disease, severe pulmonary hypertension, systolic blood pressure ≤90 mmHg or >160 mmHg, severe ventricular arrhythmia, cardiac surgery or a cerebrovascular event within the previous six months, claustrophobia or pregnant female subjects. All patients provided witnessed written consent.

Patients were randomly assigned to three groups, treated with placebo or rhNRG-1 (0.6 or 1.2 μg/kg/day) for 10 consecutive days, after finishing the day 11 follow up, they were discharged from the hospital. Another two on site follow up were at day 30 and day 90. Blood samples of each patient were collected before treatment and at day 11, 30 and 90. Plasma NT-proBNP was tested in the core lab with NT-proBNP assays (kit from Biomedica). One year after the last patient enrolled, the telephone interview was made for collecting the information of re-hospitalizations, all telephone interviews were recorded in a special form with investigators signature.

Of the 48 patients with available re-hospitalization information in the placebo group, 12 (25.0%) were rehospitalized for worsening heart failure at least once. For the 0.6 μg/kg group, only 4 (8.7%) of the 46 patients readmitted to the hospital (P=0.05 compared to placebo); Rehopitalization rate of the 1.2 μg/kg group was 22.0% (11/50). The average times of re-hospitalizations was 0.458 (22/48) per patient in the placebo group, while they were reduced by 57.4% and 17.0% respectively in the 0.6 (8/41) and 1.2 μg/kg group (19/50).

In the placebo group, the NT-proBNP were almost the same during the study while compare to the baseline. At day 11, the NT-proBNP was significantly increased in rhNRG-1 treated groups (from 1853+1512 to 2399+1841 fmol/ml in 0.6 μg/kg group, P≤0.01; from 1562±1275 to 2774±1926 fmol/ml in 1.2 μg/kg group, P≤0.01). But his increase was transient and was not caused by a worsening heart function as the cardiac function shown to be increased, the NT-proBNP decreased to the baseline level at Day 30 and Day 90 in the 1.2 μg/kg group. Moreover, in the 0.6 μg/kg group, the NT-proBNP was significantly reduced at day 30 (1323+1124 fmol/ml, P=0.01) and day 90 (1518+1403 fmol/ml, P=0.01) while compare to the baseline.

These results showed that rhNRG-1 treatment can reduce the re-hospitalizations and the plasma level of NT-proBNP, which may indicate rhNRG-1 can provide long-term benefits to chronic heart failure patients.

Example 3: A Randomized, Double-Blinded, Multi-Center, Placebo Controlled Survival Study of Recombinant Human Neuregulin 1 in Patients with Chronic Heart Failure Based on Standard Treatment To evaluate the efficacy of recombinant human neuregulin-1 for injection on chronic heart failure, a phase II, double-blinded, multi-center, placebo controlled, standard treatment based study was carried out in multiple clinical centers in China. A total of 351 patients with NYHA Class III or IV stable chronic heart failure were enrolled and randomized into placebo group or rhNRG-1 group (0.6 μg/kg). There were no significant variations in demographics or background therapies among groups. According to the schedule, patients were administered with the drug for 10 consecutive days in the hospital, after finishing the day 11 follow up, they were discharged from the hospital, and were administered with the drug once weekly from the 3rd week till the 25th week as out-patient. Blood samples of each patient were collected before treatment (baseline) and at each follow up. Plasma NT-proBNP level was tested in the core lab with NT-proBNP assays (kit from Biomedica). The survival information was collected at 52th week of the study.

Investigational Product:

Specification: Neucardin™, 61 amino acid polypeptide comprises the EGF-like domain of Neuregulin-1 β2 isoform, with the molecular weight of 7054 Dal (lug=0.14 nmol). 250 μg (5000 EU)/vial (lug-20 EU).

Preparation: For injection.

Mode of administration: Intravenously drip or infusion.

Storage: in safe place, with limited access and protected from light, at 3-8° C.

Placebo:

Specification: Excipient for Neucardin™. 250 μg/vial and without active recombinant human neuregulin-1 protein.

Dosage and regimens:

| | Day 1-10 | Week 3-25 |
|---|---|---|
| Dose | 0.6 μg/kg/day rhNRG-1 or placebo | 0.8 μg/kg/day rhNRG-1 or placebo |
| Route | Intravenous drip | Intravenous infusion |
| regimen | 10 hours per day for 10 days | 10 minutes infusion weekly |

Criteria for participation in the trial included patients with CHF (NYHA class III or IV) between the ages of 18 and 80 years old, LVEF≤40%, in relatively stable clinical condition (including clinical signs, symptoms and accepted standard treatment for CHF at the target dose or maximum tolerance dose for over 1 month). Major exclusion criteria included acute myocardial infarction, hypertrophic cardiomyopathy, constrictive pericarditis, significant valve disease or congenital heart disease, severe pulmonary hypertension, systolic blood pressure ≤90 mmHg or >160 mmHg, severe ventricular arrhythmia, cardiac surgery or a cerebrovascular event within the previous six months, claustrophobia or pregnant female subjects. All patients provided witnessed written consent.

The all-cause mortality of the placebo group at 52 week is 15.91%, with 28 death in 176 patients, while the number is 9.71% in rhNRG-1 group, with 16 death in 175 patients completed the trial (Hazard ratio=0.425, 95% CI 0.222-0.813, p=0.0097). Considering the mortality caused by cardiovascular events, the number of the placebo group at 52 week is 14.77%, with 26 death in 176 patients, and 9.71% in the rhNRG-1 group. So from the results we can find around 40% decrease of the mortality of rhNRG-1 administration compared with placebo group, even the placebo group were still maintain their previous standard treatment for chronic heart failure.

We also analyzed the all-cause mortality based on the stratification of baseline NT-proBNP. When the NT-proBNP level is stratified into 3 stratums as ≤1600 fmol/ml, >1600 fmol/ml and ≤4000 fmol/ml, or >4000 fmol/ml, the mortality of rhNRG-1 group vs placebo group are 1.49% vs 8.49%, 8.96% vs 23.33%, and 26.67% vs 28.00%, respectively. And if the NT-proBNP level is stratified as ≤4000 fmol/ml or >4000 fmol/ml, the mortality of rhNRG-1 group vs placebo group are 5.22% vs 14.89% (p=0.0092), and 26.67% vs 28.00%, respectively. These results show statistical significance that rhNRG-1 can effectively improve the survival of chronic heart failure patients.

Further, the patients were stratified with their baseline NYHA heart function class, to be class III or class IV. The all-cause mortality of class III patients in rhNRG-1 group or placebo group is 6.06% (8 death in 132 patients) and 15.49% (22 death in 142 patients), respectively, p=0.0189. While the all-cause mortality of class IV patients in rhNRG-1 group or placebo group is 20.93% (9 death in 43 patients) and 17.65% (6 death in 34 patients), respectively, p=0.778.

What is claimed is:

1. A method of treating a heart failure patient by neuregulin 1, the method comprising administering neuregulin 1 at an amount of 0.6 or 1.2 ug/kg to the heart failure patient; wherein the patient has been identified for treatment by neuregulin 1 based on a companion diagnostic test; wherein the neuregulin 1 comprises the amino acid sequence of SEQ ID NO: 1.

2. The method of claim 1, wherein the companion diagnostic test measures the plasma level of NT-proBNP in the patient.

3. The method of claim 2, wherein the result of the test is indicative for the treatment by neuregulin 1 when the plasma level of NT-proBNP≤4000 fmol/ml.

4. The method of claim 2, wherein the result of the test is indicative for the treatment by neuregulin 1 when the plasma level of NT-proBNP is between 1600 fmol/ml and 4000 fmol/ml.

5. The method of claim 2, wherein the result of the test is indicative for the treatment by neuregulin 1 when the plasma level of NT-proBNP is ≤1600 fmol/ml.

6. The method of claim 2, wherein the plasma level is measured by immunoassay.

7. The method of claim 1, wherein the companion diagnostic test is evaluating heart function by NYHA heart function classification.

8. The method of claim 2, wherein the result of the test is indicative for the treatment by neuregulin 1 when the heart function is NYHA class II or III.

* * * * *